United States Patent

Castro et al.

[11] Patent Number: 6,113,888
[45] Date of Patent: Sep. 5, 2000

[54] SELF-TANNING MOUSSE

[75] Inventors: Mauricio Castro, Rancho Palos Verdes; Frederick W. Woodin, Jr., Pacific Palisades, both of Calif.

[73] Assignee: Neutrogena Corporation, Los Angeles, Calif.

[21] Appl. No.: 09/333,445

[22] Filed: Jun. 15, 1999

[51] Int. Cl.[7] .............................. A61K 7/42; A61K 7/44; A61K 7/00

[52] U.S. Cl. .............................. 424/59; 424/60; 424/400; 424/401

[58] Field of Search .............................. 424/59, 60, 400, 424/401

[56] References Cited

U.S. PATENT DOCUMENTS

| | | | |
|---|---|---|---|
| 5,138,043 | 8/1992 | Polovsky et al. | 536/17.9 |
| 5,318,774 | 6/1994 | Alban et al. | 424/59 |
| 5,458,872 | 10/1995 | Durand | 424/59 |
| 5,620,681 | 4/1997 | Takata et al. | 424/59 |
| 5,626,839 | 5/1997 | Scales-Medeiros | 424/59 |
| 5,662,890 | 9/1997 | Punto et al. | 424/59 |
| 5,741,480 | 4/1998 | Ascione | 424/59 |

OTHER PUBLICATIONS

Herbal Self Tanning Foam Medium Dark, photocopy of package 1997.
Banana Boat Sunless Tanning Mousse Soft Medium Blend, photocopy of package 1998.
Banana Boat Tanning Mousse Deep Dark Blend, photocopy of package 1998.
Reiger, Martin M., Rhein, Linda D., "Surfactants in Cosmetics", vol. 8, Second Edition:70–81..

*Primary Examiner*—Shelley A. Dodson
*Attorney, Agent, or Firm*—William E. McGowan

[57] ABSTRACT

The present invention relates to composition comprising a self-tanning agent, a nitrogen-free polymer, and a nitrogen-free surfactant; cosmetologic products such as mousses comprising such composition and a cosmetically acceptable carrier; and methods of using such products.

24 Claims, No Drawings

SELF-TANNING MOUSSE

FIELD OF THE INVENTION

The present invention relates to a self-tanning composition comprising a non-nitrogen polymer and a non-nitrogen surfactant.

BACKGROUND OF THE INVENTION

Because of the risks associated with sun tanning such as sunburn, many people use self-tanning compositions as a means to either achieve a tan without exposure to the sun, obtain a deeper tan with less exposure to the sun, or to extend the natural life of their suntan. One of the major consumer dissatisfactions with current self-tanning products is that the products take too long to dry because many are emulsions containing a lipophilic phase. This long drying period both creates the risk of uneven skin color, as wet areas can be accidentally rubbed off, and delays the development of the artificial tanning effect.

In response to these concerns, companies have recently made aerosol and non-aerosol mousses (i.e., foams) containing self-tanning compositions, e.g., Banana Boat's Sunless Tanning Mousse and Hawaiian Tropics Self-tanning Foam. These formulations, however, contain foam-boosting ingredients that are nitrogen-containing compounds, e.g., betains, alkanolamides, alkanolamines, amine oxides, zwitterionic surfactants, and proteins. Such nitrogen-containing compounds are highly reactive with many self-tanning agents, such as 1,3-dihydroxyacetone and 1,3,4-trihydroxy butanone.

The present invention relates a novel self-tanning composition and cosmetic product (e.g., an aerosol or non-aerosol mousse) free of any predominating nitrogen chemicals classified as polymers and surfactants (e.g., which assist in the creation of the foam.

SUMMARY OF THE INVENTION

In one aspect, the invention features a composition comprising a self-tanning agent, a nitrogen-free polymer, and a nitrogen-free surfactant. In one embodiment, the composition further comprises a nitrogen-free foam booster. In one embodiment, the composition is free of ingredients containing reactive nitrogen atoms. Examples of nitrogen-free polymers (e.g., to extend the duration of the mousse's foam) include water soluble polymers such as acid and esters of dimethyl copolyol (e.g., dimethylene copolyol beeswax and dimethyl copolyol lactate), cellulose polymers (e.g., cellulose, cellulose gum, and cellulose derivatives such as an alkyl cellulosic polymer such as cetyl hydroxyethylcellulose), PVM-MA decadiene crosspolymer, starches, and vegetable derived gums (e.g., guar gum). Examples of nitrogen-free surfactants include ethylene- and/ or propylene-oxide ethers of glucose (e.g., alkyl gluceths (e.g., methyl gluceths such as methyl gluceth-10 and methyl gluceth-20)), polyalkylene (e.g., polyethylene or polypropylene) ethers of an alkyl fatty alcohol, polyalkylene ethers of an alkyl fatty ester, poloxomers (e.g., poloxamer-184, poloxamer-188, poloxamer-407, and poloxamer-338), and polyethylene glycol derivatives (e.g., PEG-60 lanolin, PEG-7 glyceryl cocoate, and PEG-6 capric/carprylic glyceride). Examples of nitrogen-free foam boosters include fatty alcohol ethers of glucose such as alkyl glucosides (e.g., C1–C20 alkyl glucosides such as decyl glucoside, cocoglucoside, and butyl glucoside), cetearyl alcohol, cetyl alcohol, and decyl alcohol. In one embodiment, the nitrogen-free surfactant is methyl gluceth-20, the nitrogen-free foam booster is decyl glucoside, and the nitrogen-free polymer is cetyl hydroxyethylcellulose. Examples of self-tanning agents include 1,3-dihydroxyacetone and 1,3,4-trihydroxy-2-butanone.

In another aspect, the invention features a cosmetic product for application to the hair, skin, or nails of a subject for the purpose of tanning, coloring, and/or darkening the same comprising: (a) the above-described composition; and (b) a cosmetically acceptable carrier. In one embodiment the product is an aerosol (i.e., containing an aerosol propellant) or a non-aerosol (i.e., not containing an aerosol propellant) mousse (i.e., a mousse base or concentrate). In one embodiment, the cosmetically acceptable carrier comprises one or more of the members selected from the group consisting of acidifying agents, alkalizing agents, aerosol propellants, antimicrobial agents, antioxidants, buffering agents, chelating agents, coloring additives, dermotologicaly active agents, dispersing agents, emollients, emulsifying agents, humectants, fragrances, preservatives, sugars, sunscreen agents, surfactants, suspending agents, thickening agents, and vehicles.

In another embodiment, the mousse comprises by weight: about 0.001% to about 30% (e.g., about 0.1% to about 10%) of a self-tanning agent; about 0.01% to about 10% (e.g., about 0.1% to about 5%) of a nitrogen-free polymer; about 0.01% to about 35% (e.g., about 0.1% to about 10%) of a nitrogen-free surfactant; about 0.01% to about 35% (e.g., about 0.1% to about 10%) of a nitrogen-free foam booster, and water (e.g., once other agents, if any, are added, QS to 100%). In a further embodiment, the mousse comprises by weight: about 0.001% to about 10% dihydroxyacetone; about 0.001% to about 10% 1,3,4-trihydroxy-2-butanone; about 0.001% to about 5% of cetyl hydroxyethylcellulose; about 0.001% to about 15% of methyl gluceth 20; about 0.001% to about 15% of decyl glucoside; and water.

In one embodiment, the mousse further comprises by weight: about 0.001% to about 50% of a humectant; about 0.001% to about 10% of an acidifying agent; and about 0.001% to about 10% of a buffer. In a further embodiment, the mousse comprises by weight: about 0.001% to about 20% of a member selected from the group consisting of glycerin, 1,2,-pentandiol, 2-methyl-1,3,-propanediol; about 0.001% to 5% of citric acid; and about 0.001% to about 10% of sodium citrate. In a further embodiment, the mousse comprises about 0.001% to about 20% of glycerin; about 0.001% to about 20% of 1,2,-pentandiol; about 0.001% to about 20% of 2-methyl-1,3,-propanediol; about 0.001% to about 5% of a paraben (e.g., methylparaben, ethylparaben, propylparaben, or butylparaben); about 0.001% to about 5% of fragrance; and about 0.001% to about 5% of PPG-5 Ceteth-20.

In another aspect, the invention features method of tanning, coloring, and/or darkening the hair, skin, or nails of a subject (e.g., a human), said method comprising applying to the same an effective amount of the above mentioned composition and mousse.

Other features and advantages of the present invention will be apparent from the detailed description of the invention and from the claims

DETAILED DESCRIPTION OF THE INVENTION

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference.

The present invention relates to a composition comprising a self-tanning agent, a nitrogen-free polymer, and a nitrogen-free surfactant. The polymer and surfactant, thus, help stabilize the active self-tanning agent (e.g., 1,3-dihydroxyacetone and/or 1,3,4-trihydrocy-2-butane) as well as, in conjunction with water, produce a strong foam.

What is meant by self-tanning agent is a chemical agent capable of producing or inducing the artificial tanning process of the skin by forming brown pigments in the skin, e.g., through the Maillard reaction reported in Bobin, et al., J. Soc. Cosmet. Chem., 35:265–72 (1984). Examples of self-tanning agents include alloxan, methyl glyoxal, ethoxydiglycol, glyceraldehyde, various indoles and imidazoles and their derivatives, pigmentation agents such as methoxselen and trioxselan, and α-hydroxy ketones and aldehydes such as , e.g., of the formula:

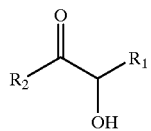

wherein $R_1$ is H, $CH_2OH$, $CHOHCH_2OH$, $CH(OH)CH(=O)$, $CH(NH_2)CH(=O)$, $CH(OCH_3)CH(=O)$, or $CH(NH-Phenyl)CH(=O)$; and $R_2$ is H or $CH_2OH$. An example of a compound of such formula is 1,3-dihydroxyacetone (i.e., dihydroxyacetone) and 1,3,4-trihydroxy-2-butanone (i.e., erythrulose).

In one aspect, the invention features a cosmetic product for application to hair, skin, and nails of a subject comprising a cosmetically acceptable carrier. The individual components of the carrier are numerous and varied, but are also well known to one skilled in the art. In one aspect, the carrier comprises one or more of the members selected from the group consisting of acidifying agents, alkalizing agents, aerosol propellants, antimicrobial agents, antioxidants, buffering agents, chelating agents, coloring additives, dermotologicaly active agents, dispersing agents, emollients, emulsifying agents, humectants, fragrances, preservatives, sugars, sunscreen agents, surfactants, suspending agents, thickening agents, an vehicles. These ingredients are discussed below. Examples of these agents are listed below as well as in the International Cosmetic Ingredient Dictionary and Handbook, eds. Wenninger and McEwen (The Cosmetic, Toiletry, and Fragrance Assoc., Washington, D.C., 7$^{th}$ Edition, 1997) (hereinafter "ICT Handbook").

When formulating the composition with these ingredients, ones containing metal oxides and active nitrogen groups, e.g., active amine groups, should be avoided when using reactive self-tanning agents (e.g., dihydroxyacetone). Furthermore, agents that interfere with the Maillard reaction should also not be used.

Acidifying and alkalizing agents are added to obtain the desired pH of the composition. Examples of acidifying agents included citric acid, lactic acid, glycolic acid, acetic acid, glacial acetic acid, malic acid, and proprionic acid. Examples of alkalizing agent include edetol, potassium carbonate, potassium hydroxide, sodium borate, sodium carbonate, sodium citrate, sodium lactate, sodium glycolate, and sodium hydroxide. Other acidifying and alkalizing agents are listed on page 1653 of the ICT handbook.

Aerosol propellants are used when the composition is to be administered as an aerosol under pressure. Examples of aerosol propellants include halogenated hydrocarbons such as dichlorodifluoromethane, dichlorotetrafluoroethane, and trichloromonfluoromethane, nitrogen, and volatile hydrocarbons such as butane, propane, isobutane, or mixtures thereof. Other aerosol propellants are listed on page 1655 of the ICT handbook.

Antimicrobial agents are used when the area that the composition is to be applied is prone to microbial infection, e.g., by bacteria, fungal, or protozoa. Examples of such agents include benzyl alcohol, chlorobutanol, phenylethyl alcohol, phenylmercuric acetate, potassium sorbate, and sorbic acid, benzoic acid, butylparabenm, ethylparaben, methylparaben, propyl paraben, and sodium benzoate. Other antimicrobial agents are listed on page 1612 of the ICT handbook.

Antioxidants are used to protect ingredients of the composition from oxidizing agents that are included within or come in contact with the composition. Examples of antioxidants include water soluble antioxidants such as grape seed extract, camellia oleifera extract, N-acetyl-L-cysteine, ascorbic acid, sodium sulfite, sodium formaldehyde, isoascorbic acid, cysteine hydrochloride, 1,4-diazobicyclo-(2,2,2)-octane, and mixtures thereof. Examples of oil-soluble antioxidants include ascorbyl palmitate, butytlated hydroxyanisole, butylated hydroxytoluene, potassium propyl gallate, octyl gallate, dodecyl gallate, phenyl-α-napthyl-amine, and tocopherols such as α-tocopherol. Other antioxidants are listed on pages 1612–13 of the ICT Handbook.

Buffering agents are used to maintain an established pH of the composition. Examples of sodium citrate, buffering agents included calcium acetate, potassium metaphosphate, potassium phosphate monobasic, and tataric acid. Other buffering agents are listed on page 1612 of the ICT handbook.

Chelating agents are used to maintain the ionic strength of the composition and/or bind to destructive compounds and metals that are included within or come in contact with the composition. Examples of chelating agents included edatate dipotassium, edetate disodium, edetic acid, and ethylenediamine tetracetic acid (EDTA) and its salts (e.g., tetrasodium EDTA). Other chelating agents are listed on page 1626 of the ICT handbook.

Coloring additives are used to add color to the composition in order to help the user identify the area in which the composition has been applied and/or modify the tanning color produced by the self-tanning agent in the composition. Examples of such coloring additives include caramel, carmine, fluorescein derivatives, methoxsalen, trioxsalen, carbon black, azo dyes, anthraquinone dyes, blue azulenes, guajazulene, chamuzulene, erythrosin, bengal rose, phloxin, cyanosin, daphinin, eosin G, cosin 10B, and Acid Red 51. Other coloring additives are listed on page 1628–30 of the ICT handbook. As discussed above, it is preferred not to use coloring additives which contain nitrogen or metals.

Dermatologically active agents include agents for treating wound healing, inflammation, acne, psoriasis, cutaneous aging, skin cancer, impetigo, herpes, chickenpox, dermatitis, pain, itching, and skin irritation. Examples of such dermatologically active agents include hydrocortisone, dexamethesone, panthenol, phenol, tetracycline hydrochloride, yeast, hexylresorcinol, lamin, kinetin, betamethasone, triamcinolone, fluocinolone, methylprednisolone, retinoids such as retinol and retinoic acid, dapsone, sulfasalazine, resorcinol, salicylic acid, benzoyl peroxide, erythromycin-benzoyl peroxide, erythromycin, clindamycin, mupirocin, griseofulvin, azoles such as miconazole, econazole, itraconazole, fluconazole, and ketoconazole, ciclopirox, allylamines such as naftifine and terfinafine, acyclovir, famciclovir, valacyclovir, benzocaine, lidocaine, dibucaine, pramoxine hydrochloride, methyl salicylate, camphor, menthol, resocinol, and vitamins such as tocopherol, tocopheryl acetate, pantothenic acid, panthenol, ascorbic acid, biotin, and retinoids such as retinol, retinoic acid, retinal, retinyl acetate, and retinyl palmitate, $\alpha$-hydroxy acid, a $\beta$-hydroxy acid, or polyhydroxy acid such as glycolic acid, lactic acid, citric acid, malic acid, and azaleic acid Examples of dispersing and suspending agents include poligeenan, magnesium aluminum silicate, and silicon dioxide. Other dispersing or suspending agents are listed on page 1612 of the ICT handbook.

Emollients are agents which soften and smooth the skin. Examples of emollients include hydrocarbon oils and waxes such as mineral oil, petrolatum, microcrystaline wax, polyethylene, triglyceride esters such as those of castor oil, cocoa butter, safflower oil, cottonseed oil, corn oil, olive oil, cod liver oil, almond oil, avocado oil, palm oil, sesame oil, squalene, and soybean oil, acetylated monoglycerides, ethoxylated glycerides, fatty acids, alkyl esters of fatty acids, alkyl esters of benzoic acid (e.g., benzoates), alkenyl esters of fatty acids, fatty alcohols, fatty alcohol ethers, etheresters, lanolin and derivatives of lanolin, polyhydric alcohol esters, wax esters such as beeswax, vegetable waxes, phospholidds, and sterols. Other emollients are listed on pages 1656–61 of the ICT handbook.

Emulsifying agents are used for preparing the oil-in-water emulsions of the present invention. Examples of emulsifying agents include polyethelene and/or polypropylene fatty esters/ethers of glucose (e.g., methyl gluceth sesquisterate). Other emulsifiers are listed on pages 1679–87 of the ICT Handbook. Emulsion stabilizers are listed on pages 1634–35 of the ICT Handbook.

Foam boosters are used to increase the foaming capacity of surfactants or to stabilize foams in general. Foam boosters generally increase the surface viscosity of the liquid that surrounds the individual bubbles in a foam/mousse. Examples of foam boosters (e.g., nitrogen-free foam boosters) are listed on pages 1686–87 of the ICT Handbook.

Humectants are agents which promote the retention of moisture, e.g., moisturizers. Examples of humectants include sorbitol, glycerin, glycereth 5 lactate, glycereth 7 triacetate, glycereth 7 diisononoate, hexanetriol, glycols such as 2-methyl-1,3-propanediol, 1,2-pentanediol, hexylene glycol, and propylene glycol, alkoxylated glucose, D-panthenol and derivatives thereof, and hyaluronic acid. Other humectants are listed on pages 1661–62 of the ICT Handbook.

Examples of fragrances include peppermint, rose oil, rose water, aloe vera, clove oil, menthol, camphor, eucalyptus oil, and other plant extracts. Certain fragrances may require a solubilizer, e.g., PPG-5-ceteth-20. To eliminate certain odors from compositions, masking agents may be used. An example of a masking agent includes ethylene brassylate. Other fragrances and masking agents are listed on pages 1639–40 of the ICT Handbook.

Preservatives are used to protect the composition from degradation. Examples of preservatives include phenoxyethanol, benzoic acid, benzyl alcohol, parabens such as methylparaben, propylparaben, butylparaben, isopropylparaben, and isobutylparaben, diazolidinyl urea, imidazolidinyl urea, diazolindyl urea, benzalkonium chloride, benzethonium chloride, phenol, and mixtures thereof (e.g., the paraben mixture Liquipar Oil™ and Phenonip™). Other preservatives are listed on pages 1654–55 of the ICT Handbook.

Sugars are used to improve the results obatined by the self-tanning agents. Examples of sugars include monosaccharides, disaccharides, and polysccharides such as glucose, xylose, fructose, reose, ribose, pentose, arabinose, allose, tallose, altrose, mannose, galactose, lactose, sucrose, erythrose, glyceraldehyde, or any combination thereof.

Sunscreen agents are agents used to screen or reduce the amount of ultraviolet radiation impinging on the skin (e.g., by absorption, scattering, and reflection of the ultraviolet radiation). Segarin, et al., Cosmetics Science and Technology, Chapter VIII, pages 189, et seq. discloses numerous examples of sunscreen agents. Examples of sunscreen agents include both organic compounds and their salts such as phenylbenzimidazole sulfonic aicd, octyl methoxycinnamate, octyl salicylate, benzophenones such as benzophenone-3, homosalate, octocrylene, avobenzone, and menthyl anthranilate, as well as inorganic particulate materials such as zinc oxide and titanium dioxide. Other sunscreen agents are listed on page 1672 of the ICT Handbook. Generally, the composition will contain from about 1% to about 50%, by weight, of sunscreen agent(s). The exact amounts will vary depending on the sunscreen used and the desired sun-protection factor (SPF), e.g., and SPF of at least 4 or an SPF of at least 15.

Surfactants are agents used to stabilize multi-component compositions, e.g., used as wetting agents, emulsifiers, dispersing agents, and penetrants. Examples of surfactants include alkene oxide, ethers of fatty alcohols, glucose, and sorbitol, methyl gluceth 20, decyl glucoside, laureth 4, laureth 9, monoethanolamine, nonoxynol 4, nonoxynol 9, nonoxynol 10, nonoxynol 15, nonoxynol 30, poloxalene, polyoxyl 8, 40, and 50 stearate, polysorbate 20, polysorbate 40, polysorbate 60, polysorbate 65, polysorbate 80, and polysorbate 85, sodium lauryl sulfate, PPG-5 ceteth-20, and sorbitan and its derivatives. Other surfactants are listed on page 1672–90 of the ICT Handbook.

Vehicles are often referred to as the base for the cosmetically acceptable carrier, e.g., a fluid that is capable of delivering the other components of the composition to the skin with acceptable absorption of those components into the skin. Examples of vehicles include water (e.g., deionized water), oil-in-water emulsions (e.g., where the continuous water phase contains the water soluble agents and the discontinuous oil phase contains the oil soluble agents), and water-in-oil emulsions (e.g., where the continuous oil phase contains the oil soluble agents and the discontinuous water phase contains the water soluble agents). The oil phase may be established by the addition of animal/vegetable derived oils, esters, and ethers, and hydrocarbon and/or silicone solvents, e.g., dimethicone and/or cyclomethicone, together with various emulsifying agents. Oil-in-water emulsions (e.g., ratio of about 10:1 to about 1:100 such as about 1:1 to about 1:10) may be used in preparing mousses.

Typically, the viscosity of a mousse formulations of the present invention will range up to 200 cps. Bulking agents may be used to increase the viscosity of the composition. Viscosity decreasing agents are listed on pages 1692–92 of the ICT Handbook.

The composition or product the present invention may be prepared using methodology that is well known by an artisan of ordinary skill (e.g., by using well-known mixing and blending procedures). For example, emulsion products of the present invention, each phase of the emulsion may be separately prepared with all of the components contained in their appropriate phases. The emulsion is then formed by adding one phase to the other phase with agitation.

The composition or product of the present invention may be packaged in a container that is well known by an artisan of ordinary skill. For example, non-aerosol mousses of the present invention can use the Non-aerosol Finger-pump with a polyethylene or PVC container sold by Air Supply, Pompano Beach, Fla. Aerosol mousses of the present invention can use, for example, aluminum containers having an aerosol nozzle.

The composition of the present invention may be prepared using methodology that is well known by an artisan of ordinary skill. The following is a description of the manufacture of two compositions/mousses of the present invention. Other compositions/mousses of the invention can be prepared in an analogous manner by a person of ordinary skill in the art.

EXAMPLE 1

The weight percentage of the ingredients of the mousse of this Example 1 are recited below in Table 1.

TABLE 1

| INGREDIENTS | Weight (%) |
|---|---|
| Step A | |
| WATER | 59.20 |
| CETYL HYDOXYETHYLCELLULOSE | 0.50 |
| Step B | |
| WATER | 25.00 |
| CITRIC ACID | 0.20 |
| SODIUM CITRATE | 0.35 |
| DIHYDROXYACETONE | 6.00 |
| ERYTHRULOSE | 0.75 |
| Step C | |
| METHYL GLUCETH 20 | 1.00 |
| GLYCERIN | 1.00 |
| 1,2-PENTANDIOL | 3.00 |
| 2-METHYL-1,3-PROPANEDIOL | 0.50 |
| DECYL GLUCOSIDE | 1.00 |
| PHENONIP ™ | 0.30 |
| PPG-5 CETETH | 1.00 |
| Step D | |
| FRAGRANCE | 0.20 |

The water and cetyl hydroxyethylcellulose (Natrosol Plus CS 300, Hercules Incorporated, Wilmington, Del.) of Step A were mixed and heated up to 70° C. The mixture was maintained at 70° C. until the polymer was completely hydrated ("Step A Mixture"). The water, citric acid, and sodium citrate of Step B were added, and the mixture was mixed and cooled until the citric acid and sodium citrate dissolved. Once the temperature reached below 40° C., the dihydroxyacetone (Rona, Hawthorne, N.Y.) and erythrulose (Pentapharm, Ltd., Basel, Switzerland) were added to the mixture ("Mixture AB").

All of the ingredients of Step C were mixed together in a mixer. Methyl gluceth 20 was obtained from Amerchol Corp (Edison, N.J.) as Glucam E-20, 1,2-pentandiol was obtained from Dragoco (Totowa, N.J.) as Hydrolite-5, 2-methyl-1,3-propanediol was obtained from Lyondell (Newtown, Pa.) as MP Diol Glycol, decyl glucoside was obtained from Henkel Corp. (Amber, Pa.) as Plantaren 2000, Phenonip™ (a blend of phenoxyethanol, methylparaben, ethylparaben, propylparaben, and butylparaben) was obtained from NIPA Corp.(Williamstown, Del.), and PPG-5 Cetearth-20 was obtained from Croda Corp (Parsippany, N.J.) as Procetyl AWS. Once a homogenous solution was achieved, the fragrance was added. The mixture was stirred well until the fragrance was dissolved ("Mixture CD"). Mixture CD was then added to Mixture AB, and the resulting mixture was mixed well. The resulting self-tanning mousse has a pH of 4–4.8.

EXAMPLE 2

The weight percentage of the ingredients of the mousse of this Example 2 are recited below in Table 2.

TABLE 2

| INGREDIENTS | Weight (%) |
|---|---|
| Step A | |
| WATER | 60.45 |
| CETYL HYDOXYETHYLCELLULOSE | 0.50 |
| Step B | |
| WATER | 25.00 |
| CITRIC ACID | 0.20 |
| SODIUM CITRATE | 0.35 |
| DIHYDROXYACETONE | 5.00 |
| ERYTHRULOSE | 0.50 |
| Step C | |
| METHYL GLUCETH 20 | 1.00 |
| GLYCERIN | 1.00 |
| 1,2-PENTANDIOL | 3.00 |
| 2-METHYL-1,3-PROPANEDIOL | 0.50 |
| DECYL GLUCOSIDE | 1.00 |
| PHENONIP ™ | 0.30 |
| PPG-5 CETETH-20 | 1.00 |
| Step D | |
| FRAGRANCE | 0.20 |

The water and cetyl hydroxyethylcellulose of Step A were mixed and heated up to 70° C. The mixture was maintained at 70° C. until the polymer was completely hydrated (Step A Mixture). The water, citric acid, and sodium citrate of Step B were added. The mixture was mixed and cooled until the citric acid and sodium citrate dissolved. Once the temperature reached below 40° C., the dihydroxyacetone and erythrulose were added to the mixture ("Mixture AB").

All of the ingredients of Step C were mixed together in a mixer. Once a homogenous solution was achieved, the fragrance was added. The mixture was stirred well until the fragrance was dissolved ("Mixture CD"). Mixture CD was then added to Mixture AB, and the resulting mixture was mixed well. The resulting self-tanning mousse has a pH of 4–4.8.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A single water phase composition comprising a self-tanning agent, a nitrogen-free polymer, a nitrogen-free surfactant, and water.

2. A composition of claim 1, wherein said composition further comprises a nitrogen-free foam booster.

3. A composition of claim 2, wherein said composition does not comprise any ingredients containing a nitrogen.

4. A composition of claim 3, wherein said nitrogen-free polymer is selected from the group consisting of cellulose, a cellulose derivative, and a vegetable derived gum, said nitrogen-free surfactant is selected from the group consisting of an alkyl gluceth, a poloxomer, a polyalkylene ether of an alkyl fatty alcohol, and a polyalkylene ether of an alkyl fatty ester, and said nitrogen-free foam booster is selected from the group consisting of an alkyl glucoside, cetearyl alcohol, and cetyl alcohol.

5. A composition of claim 4, wherein said nitrogen-free surfactant is methyl gluceth-20, said nitrogen-free polymer is cetyl hydroxyethylcellulose, and said nitrogen-free foam booster is decyl glucoside.

6. A composition of claim 2, wherein said self-tanning agent is selected from the group consisting of 1,3-dihydroxyacetone and 1,3,4-trihydroxy-2-butanone.

7. A composition of claim 3, wherein said self-tanning agent is selected from the group consisting of 1,3-dihydroxyacetone and 1,3,4-trihydroxy-2-butanone.

8. A composition of claim 3, wherein said composition comprises 1,3-dihydroxyacetone and 1,3,4-trihydroxy-2-butanone.

9. A composition of claim 5, wherein said composition comprises 1,3-dihydroxyacetone and 1,3,4-trihydroxy-2-butanone.

10. A mousse for application to the hair, skin, or nails of a subject for the purpose of tanning, coloring, and/or darkening the same comprising a self-tanning agent, a nitrogen-free polymer, and a nitrogen-free surfactant, and a cosmetically acceptable carrier, wherein said cosmetically acceptable carrier comprises water.

11. A mousse of claim 10, wherein said mouse further comprises a nitrogen-free foam booster.

12. A mousse of claim 11, wherein said mousse does not comprise any ingredients containing a nitrogen.

13. A mousse of claim 12, wherein said nitrogen-free polymer is selected from the group consisting of cellulose, a cellulose derivative, and a vegetable derived gum, said nitrogen-free surfactant is selected from the group consisting of an alkyl gluceth, a poloxomer, a polyalkylene ether of an alkyl fatty alcohol, and a polyalkylene ether of an alkyl fatty ester, and said nitrogen-free foam booster is selected from the group consisting of an alkyl glucoside, cetearyl alcohol, and cetyl alcohol.

14. A mousse of claim 13, wherein said nitrogen-free surfactant is methyl gluceth-20, said nitrogen-free polymer is cetyl hydroxyethylcellulose, and said nitrogen-free foam booster is decyl glucoside.

15. A mousse of claim 14, wherein said composition comprises 1,3-dihydroxyacetone and 1,3,4-trihydroxy-2-butanone.

16. A mousse of claim 11, wherein said cosmtologically acceptable carrier comprises one or more of the members selected from the group consisting of acidifying agents, alkalizing agents, aerosol propellants, antimicrobial agents, antioxidants, buffering agents, chelating agents, coloring additives, dermotologicaly active agents, dispersing agents, emollients, emulsifying agents, humectants, fragrances, preservatives, sugars, sunscreen agents, surfactants, suspending agents, thickening agents, and vehicles.

17. A mousse of claim 16, wherein said mousse comprises by weight:
 (a) about 0.001% to about 30% of a self-tanning agent;
 (b) about 0.01% to about 10% of a nitrogen-free polymer;
 (c) about 0.01% to about 35% of a nitrogen free surfactant;
 (d) about 0.01% to about 35% of a nitrogen free foam booster; and
 (e) water.

18. A mousse of claim 17, wherein said mousse further comprises by weight:
 (f) about 0.001% to about 50% of a humectant;
 (g) about 0.001% to about 10% of an acidifying agent; and
 (h) about 0.001% to about 10% of a buffer.

19. A mousse of claim 16, wherein said mousse comprises by weight:
 (a) about 0.001% to about 10% dihydroxyacetone;
 (b) about 0.001% to about 10% 1,3,4-trihydroxy-2-butanone;
 (c) about 0.01% to about 5% of cetyl hydroxyethylcellulose;
 (d) about 0.01% to about 15% of methyl gluceth 20;
 (e) about 0.01% to about 15% of decyl glucoside; and
 (f) water.

20. A mousse of claim 19 wherein said mousse comprises by weight:
 (g) about 0.001% to about 20% of a member selected from the group consisting of glycerin, 1,2,-pentandiol, 2-methyl-1,3,-propanediol;
 (h) about 0.001% to 5% of citric acid; and
 (i) about 0.001% to about 10% of sodium citrate.

21. A mousse of claim 20 wherein said mousse comprises by weight:
 about 0.001% to about 10% of glycerin;
 about 0.001% to about 10% of 1,2,-pentandiol; and
 about 0.001% to about 10% of 2-methyl-1,3,-propanediol.

22. A mousse of claim 21 wherein said mousse further comprises by weight:
 about 0.001% to about 0.5% of a paraben;
 about 0.001% to about 5% of fragrance; and
 about 0.001% to about 5% of PPG-5 Ceteareth-20.

23. A method of tanning, coloring, and/or darkening the hair, skin, or nails of a subject, said method comprising applying to the same an effective amount of the mousse according to claim 10.

24. A method of tanning, coloring, and/or darkening the hair, skin, or nails of a subject, said method comprising applying to the same an effective amount of the mousse according to claim 21.

* * * * *